United States Patent
Hoult

(10) Patent No.: US 10,018,561 B2
(45) Date of Patent: Jul. 10, 2018

(54) DIAMOND ATR ARTEFACT CORRECTION

(71) Applicant: PerkinElmer Singapore PTE Ltd, Singapore (SG)

(72) Inventor: Robert Alan Hoult, Beaconsfield (GB)

(73) Assignee: PERKINELMER SINGAPORE PTE LTD, Singapore (SG)

( * ) Notice: Subject to any disclaimer, the term of this patent is extended or adjusted under 35 U.S.C. 154(b) by 524 days.

(21) Appl. No.: 14/420,101

(22) PCT Filed: Jul. 23, 2013

(86) PCT No.: PCT/GB2013/000320
§ 371 (c)(1),
(2) Date: Feb. 6, 2015

(87) PCT Pub. No.: WO2014/023924
PCT Pub. Date: Feb. 13, 2014

(65) Prior Publication Data
US 2015/0177142 A1    Jun. 25, 2015

(30) Foreign Application Priority Data

Aug. 6, 2012 (GB) .................................. 1213997.8

(51) Int. Cl.
*G01N 21/62* (2006.01)
*G01J 3/28* (2006.01)
(Continued)

(52) U.S. Cl.
CPC ............... *G01N 21/62* (2013.01); *G01J 3/28* (2013.01); *G01N 21/274* (2013.01);
(Continued)

(58) Field of Classification Search
CPC ............... G01N 21/62; G01N 21/274; G01N 2201/1218; G01N 2201/12784; G01J 3/28
See application file for complete search history.

(56) References Cited

U.S. PATENT DOCUMENTS

| | | | | |
|---|---|---|---|---|
| 4,529,319 A | * | 7/1985 | Muller | ................. G01N 21/171 356/432 |
| 2007/0170362 A1 | * | 7/2007 | Patterson | ................. G01J 3/02 250/339.07 |
| 2011/0070602 A1 | | 3/2011 | Thomson et al. | |

FOREIGN PATENT DOCUMENTS

| | | |
|---|---|---|
| DE | 10 2006 036808 A1 | 2/2008 |
| EP | 1550854 A2 | 6/2005 |
| EP | 2395332 A1 | 12/2011 |

OTHER PUBLICATIONS

Kleideiter et al. Pressure dependence of thickness and refractive index of thin PMMA-films investigated by surface plasmon and optical waveguide spectroscopy. Macromol. Chem. Phys. 200, 1028-1033 (1999).*

(Continued)

*Primary Examiner* — Dominic J Bologna
(74) *Attorney, Agent, or Firm* — Heslin Rothenberg Farley & Mesiti P.C.; Victor A. Cardona, Esq.

(57) ABSTRACT

A method of using a spectrometer to produce corrected diamond Attenuated Total Reflectance (ATR) spectral data includes acquiring, using the spectrometer, an initial set of ATR spectral data for a sample pressed into contact with a diamond ATR crystals; numerically matching, using the spectrometer, a pressure dependent diamond artifact reference spectrum to a corresponding pressure dependent diamond artifact in the initial set of ATR spectral data; and numerically subtracting out the numerically matched pressure dependent diamond artifact reference spectrum from the initial set of ATR spectral data to yield a corrected set of ATR spectral data for the sample for output by the spectrometer.

25 Claims, 10 Drawing Sheets

(51) Int. Cl.
 *G01N 21/27* (2006.01)
 *G01N 21/552* (2014.01)
(52) U.S. Cl.
 CPC ... *G01N 21/552* (2013.01); *G01N 2201/1218* (2013.01); *G01N 2201/12784* (2013.01)

(56) References Cited

OTHER PUBLICATIONS

International Report on Patentability issued in connection with corresponding International Application No. PCT/GB2013/0000320, dated Feb. 10, 2015.
International Search Report for International Application No. PCT/GB2013/0000320, dated Nov. 20, 2013.

* cited by examiner

DIAMOND ATR ARTEFACT CORRECTION

CROSS REFERENCE TO RELATED APPLICATIONS

This application is a national stage filing under section 371 of International Application No. PCT/GB2013/000320, filed on Jul. 23, 2013, and published in English on Feb. 13, 2014, as WO 2014/023924 A1 and claims priority of Great Britain application GB 1213997.8 filed on Aug. 6, 2012, the entire disclosure of these applications being hereby incorporated herein by reference.

BACKGROUND

This invention relates to diamond ATR artefact correction of spectral data produced using Attenuated Total Reflectance (ATR) techniques.

SUMMARY OF THE INVENTION

The method of Attenuated Total Reflectance (ATR) has been used for many years as a simple sample interface through which infrared spectra of many materials can be obtained. Materials of interest typically exhibit strong characteristic absorption features in the range 5000-200 $cm^{-1}$ (2-50 microns). These absorption features tend to be so strong that in order to measure the features accurately by normal transmission spectroscopy samples must be thinned to an inconvenient degree to allow transmitted light to be detected. ATR has the advantage that the technique characterises just the first few microns of the sample surface making sample preparation relatively simple.

In ATR light from the spectrometer is totally internally reflected at an angle of incidence just above the critical angle at a facet of high refractive index material having little or no internal absorbance in the spectral range of interest. External to the facet this light creates an "evanescent wave"—an electric field that decays rapidly with distance from the facet. The wave can interact with any sample material brought very close to the facet, and should the material have significant optical absorbance, some of the incident light will be absorbed resulting in less light reflected from the internal surface. In this way the absorbance spectrum of the sample can be measured.

With this technique sample thickness is irrelevant but by the same token the sample must be brought into intimate contact with the facet to ensure adequate and consistent penetration depth. Typically this is achieved by applying high pressure to the sample. In turn this means that pressure is applied to the underlying optical substrate (or ATR crystal).

Diamond is a popular material for use as an ATR crystal. Diamond is a preferred material for use as ATR crystals because it is very hard and therefore easy to clean and has transmittance from UV to the very far infrared. However diamond suffers from some comparatively weak absorptions around 2400 $cm^{-1}$.

Generally speaking, these absorbance features will tend to appear in the resultant spectrum when a sample is inspected. However, techniques exist for correcting this potential error. In particular, a transmittance spectrum of the sample may be taken, and also a transmittance spectrum of the background, without a sample in position. The background spectrum will include the absorbance features of the diamond. Thus these may be removed from the sample spectrum by dividing the sample spectrum by the background spectrum.

However it has been realised by the applicants that various absorbance features exhibited by diamond in the wave number range of interest in ATR measurements are pressure dependent. That is to say, the characteristic absorbance spectrum of the diamond ATR crystal itself (which can be termed a diamond ATR artefact spectrum) varies with applied pressure.

Of course, as mentioned above, where samples (specifically non liquid samples) are to be investigated using ATR, these are pressed against the ATR crystal causing pressure to be exerted on the ATR crystal. This pressure is typically applied by a relatively simple clamping mechanism and thus the precise pressure applied can vary quite considerably.

Further in a normal spectrometer, being used in normal laboratory circumstances, there will be no convenient way to measure the pressure applied.

The artefact could in theory be eliminated by measuring the background spectrum with the same pressure on the diamond as was employed when measuring the sample spectrum. However, this is easier said than done because the pressure applied is applied through the sample. It would require a pressure transmitting medium with no optical absorbance over the measurement range to substitute the sample and even then matching the pressure adequately would be difficult.

The present invention aims at providing methods and apparatus for allowing correction for pressure dependent absorbance features exhibited by diamond ATR crystals.

According to a first aspect of the present invention there is provided a method of using a spectrometer to produce corrected diamond Attenuated Total Reflectance (ATR) spectral data comprising the steps of:

acquiring, using the spectrometer, an initial set of ATR spectral data for a sample pressed into contact with a diamond ATR crystal;

numerically matching, using the spectrometer, a pressure dependent diamond artefact reference spectrum to a corresponding pressure dependent diamond artefact in the initial set of ATR spectral data; and numerically subtracting out the numerically matched pressure dependent diamond artefact reference spectrum from the initial set of ATR spectral data to yield a corrected set of ATR spectral data for the sample for output by the spectrometer.

This provides a practical way to provide an improved set of spectral data for further analysis by correcting for a pressure dependent error introduced by the diamond ATR crystal without having to attempt to determine the pressure applied to the ATR crystal via the sample.

The numerically matching step may comprise adjusting the magnitude of the artefact reference spectrum. This allows for differences in the pressure applied to the diamond ATR crystal via the sample, since it has been found that the magnitude of the artefact is dependent on the applied pressure.

The numerically matching step may comprise adjusting for differences in abscissa scales associated with the reference spectrum and the initial set of spectral data. This can allow for the fact, for example, that the reference spectrum was determined on a different spectrometer than the one being used to produce the spectral data for the sample.

The step of adjusting the magnitude of the artefact reference spectrum may comprise finding a magnitude that yields a best fit between the pressure dependent diamond artefact reference spectrum and the corresponding pressure dependent diamond artefact in the initial set of ATR spectral data.

The step of adjusting the magnitude of the artefact reference spectrum may comprise the steps of:

i) finding a magnitude that yields a best fit between the pressure dependent diamond artefact reference spectrum and the corresponding pressure dependent diamond artefact in the initial set of ATR spectral data;

ii) identifying at least one data point from the best fit as an outlier;

iii) suppressing said at least one data point and finding a modified magnitude that yields a modified best fit between the pressure dependent diamond artefact reference spectrum and the corresponding pressure dependent diamond artefact in the initial set of ATR spectral data with said at least one data point suppressed.

This can help ensure that real features in the spectral data due to the sample are excluded from the fitting process to improve the fitting process. In effect this allows fitting based on features which are clearly part of the artefact whilst ignoring features which are not.

Steps ii) and iii) above may be iterated suppressing further data points in each iteration, and may be iterated a predetermined number of times and/or until predetermined conditions are met.

The step of adjusting the magnitude of the artefact reference spectrum may comprise determining a magnitude scale factor.

The method may comprise the step of acquiring, using the spectrometer, a set of spectrometer specific standard ATR spectral data for a standard sample substance. This is akin to taking a background reading.

The step of adjusting for differences in abscissa scales may comprise the step of:

comparing the spectrometer specific standard ATR spectral data with a reference set of standard ATR spectral data for the standard sample substance.

The standard sample substance may be diamond. In practice this means the diamond of the diamond ATR crystal.

Thus the method may comprise the step of acquiring, using the spectrometer, a set of spectrometer specific standard ATR spectral data for a standard sample substance by taking a background spectrum with the diamond ATR crystal in position but no sample in position.

The step of adjusting for differences in abscissa scales may comprise the steps of:

first adjusting for differences in abscissa scales based on the comparison between the spectrometer specific standard ATR spectral data and the reference set of standard ATR spectral data for the standard sample substance; and after this further adjusting for differences in abscissa scales based on a comparison between the pressure dependent diamond artefact reference spectrum and the corresponding pressure dependent diamond artefact in the initial set of ATR spectral data.

The numerically matching step may comprise pre-processing at least one of the sets of ATR spectral data and/or the pressure dependent diamond artefact reference spectrum to suppress slow baseline variation.

The pre-processing may comprise filtering the data. The pre-processing may comprise determining the first derivative of the data.

Pre-processing may be used as part of the step of adjusting for differences in abscissa scales and/or as part of the step of adjusting the magnitude of the artefact reference spectrum.

The step of adjusting for differences in abscissa scales may comprise the steps of:

determining an abscissa shifted version of the reference set of standard ATR spectral data;

determining a difference spectrum from the difference between the abscissa shifted version of the reference set of standard ATR spectral data and the original reference set of standard ATR spectral data;

determining a trial spectrum by adding a scaled amount of the difference spectrum to the original reference set of standard ATR spectral data, the scaled amount being characterised by a shift scale factor;

fitting the trial spectrum to the set of spectrometer specific standard ATR spectral data by varying the shift scale factor to obtain the best fit; and determining an appropriate abscissa scale adjustment in dependence on the shift scale factor corresponding to the best fit.

The above steps can be described as fitting a shift difference correction spectrum to a target spectrum. This process may be carried out using respective pre-processed spectral data/spectra, again to help reduce baseline effects.

Thus for example the step of adjusting for differences in abscissa scales may comprise the steps of:

determining an abscissa shifted version of the reference set of standard ATR spectral data;

determining a difference spectrum from the difference between the abscissa shifted version of the reference set of standard ATR spectral data and the original reference set of standard ATR spectral data;

determining the first derivative of the difference spectrum, the first derivative of the original reference set of standard ATR spectral data, and the first derivative of the set of spectrometer specific standard ATR spectral data;

determining a trial spectrum by adding a scaled amount of the first derivative of the difference spectrum to the first derivative of the original reference set of standard ATR spectral data, the scaled amount being characterised by a shift scale factor;

fitting the trial spectrum to the first derivative of the set of spectrometer specific standard ATR spectral data by varying the shift scale factor to obtain the best fit; and determining an appropriate abscissa scale adjustment in dependence on the shift scale factor corresponding to the best fit.

Further the same approach of fitting a shift difference correction spectrum to target spectrum may be used for conducting a comparison between the pressure dependent diamond artefact reference spectrum and the corresponding pressure dependent diamond artefact in the initial set of ATR spectral data to further adjust (or "fine tune") for differences in abscissa scales.

Thus for example the step of adjusting for differences in abscissa scales may comprise the steps of:

adjusting the pressure dependent diamond artefact reference spectrum in dependence on the determined abscissa scale adjustment to give an adjusted artefact reference spectrum;

determining an abscissa shifted version of the adjusted artefact reference spectrum;

determining a difference spectrum from the difference between the abscissa shifted version of the adjusted artefact reference spectrum and the original adjusted artefact reference spectrum;

determining the first derivative of the difference spectrum, the first derivative of the original adjusted artefact reference spectrum, and the first derivative of the initial set of ATR spectral data;

determining a trial spectrum by adding a scaled amount of the first derivative of the difference spectrum to the first derivative of the original adjusted artefact reference spectrum, the scaled amount being characterised by a shift scale factor;

fitting the trial spectrum to the first derivative of the initial set of ATR spectral data by varying the shift scale factor to obtain the best fit; and determining a further appropriate abscissa scale adjustment in dependence on the shift scale factor corresponding to the best fit.

The numerically matching step may comprise the step of adjusting the resolution of the diamond artefact reference spectrum to match the resolution of the initial set of ATR spectral data.

The numerically matching step may comprise the step of adjusting the diamond artefact reference spectrum by interpolating to match the sampling interval of the initial set of ATR spectral data.

The numerically matching step may comprise applying a convolution filter to the diamond artefact reference spectrum representing a difference in instrument line shape functions between the spectrometer used to determine the reference spectra and the spectrometer used in investigating the sample.

The step of adjusting the magnitude of the artefact reference spectrum may include the determination of at least one magnitude coefficient. The magnitude coefficient may comprise the magnitude scale factor.

The step of adjusting for differences in abscissa scales may include the determination of at least one shift coefficient. The shift coefficient may comprise the shift scale factor.

After the numerically matching step and before the numerically subtracting out step the method may comprise the step of checking whether the at least one magnitude coefficient satisfies at least one respective threshold.

After the numerically matching step and before the numerically subtracting out step the method may comprise the step of checking whether the at least one shift coefficient satisfies at least one respective threshold.

The step of numerically subtracting out the numerically matched pressure dependent diamond artefact reference spectrum may comprise determining the spectrum to subtract out by scaling the diamond artefact reference spectrum in dependence on the magnitude coefficient to generate a scaled diamond artefact reference spectrum;

scaling the shifted difference spectrum for the diamond artefact reference spectrum in dependence on the shift coefficient to generate a scaled shifted difference spectrum; and summing the scaled diamond artefact reference spectrum and the scaled shifted difference spectrum to generate the spectrum to be subtracted out.

The step of numerically subtracting out the numerically matched pressure dependent diamond artefact reference spectrum may comprise dividing in transmittance. This can avoid destroying any negative transmittance values.

According to a second aspect of the present invention there is provided a spectrometer arranged for performing Attenuated Total Reflectance (ATR) measurements comprising:

a source of radiation;

a detector for detecting radiation having passed through a diamond ATR crystal positioned in the spectrometer; and processing means for processing the output of the detector to produce sets of ATR spectral data;

wherein the spectrometer has a memory for storing a pressure dependent diamond artefact reference spectrum and is arranged to acquire an initial set of ATR spectral data for a sample pressed into contact with a diamond ATR crystal;

and the processing means is arranged to:

numerically match the pressure dependent diamond artefact reference spectrum to a corresponding pressure dependent diamond artefact in the initial set of ATR spectral data; and numerically subtract out the numerically matched pressure dependent diamond artefact reference spectrum from the initial set of ATR spectral data to yield a corrected set of ATR spectral data for the sample for output by the spectrometer.

Note that in general terms the spectrometer may be arranged to carry out each of the optional steps described above following the first aspect of the invention. Typically the processing means will be arranged under the control of the software to perform those steps.

The processing means may be integrated into a main body with the remainder of the spectrometer or may comprise a computer connected to the remainder of the spectrometer.

According to a third aspect of the present invention there is provided a method of producing corrected diamond Attenuated Total Reflectance (ATR) spectral data comprising the steps of:

obtaining a pressure dependent diamond artefact reference spectrum on a, first, reference spectrometer;

acquiring, using a second spectrometer, an initial set of ATR spectral data for a sample pressed into contact with a diamond ATR crystal;

numerically matching, using the second spectrometer, the pressure dependent diamond artefact reference spectrum to a corresponding pressure dependent diamond artefact in the initial set of ATR spectral data; and numerically subtracting out the numerically matched pressure dependent diamond artefact reference spectrum from the initial set of ATR spectral data to yield a corrected set of ATR spectral data for the sample for output by the second spectrometer.

The optional features described following the first aspect of the invention are also optional features of the third aspect of the invention.

According to a fourth aspect of the present invention there is provided a method of obtaining a pressure dependent diamond artefact reference spectrum for use in producing corrected diamond Attenuated Total Reflectance (ATR) spectral data, the method comprising the steps of:

providing a diamond ATR crystal in a reference spectrometer and pressing a reference sample against the ATR crystal;

varying the applied pressure with which the reference sample is pressed against the ATR crystal;

obtaining, using the reference spectrometer, spectra for the reference sample at a plurality of applied pressures;

determining pressure dependent features in the resulting spectra; determining at least one region in the spectrum exhibiting pressure dependence;

generating a pressure dependent diamond artefact reference spectrum by restricting the range of the spectrum to said at least one region and including only features determined as pressure dependent in the respective determining step.

The features of the fourth aspect of the invention may be used in the obtaining step of the third aspect of the invention.

The following features may be used as part of both the third and fourth aspects of the invention.

The reference sample may be selected as one which is spectrally featureless in the range of interest. It may be a reflective sample such as aluminium foil or transmissive such as $CaF_2$.

Numerical correlation methods may be used to determine the pressure dependent features such as Principal Components Analysis, or, assuming that the applied pressure may be independently determined, techniques such as Principal Components Regression or Partial Least Squares may be used.

The at least one region is preferably chosen to be narrow so as to minimise the risk of removing real features from the data when the reference spectrum is used.

Preferably at each end of the at least one region, the reference spectrum tends to zero so at to leave no steps in the data when the reference spectrum is used.

The method may comprise the step of obtaining spectra at a plurality of resolutions.

The method may comprise the step of also using the reference spectrometer to obtain a reference set of standard ATR spectral data for a standard sample substance.

A computer program or a computer under control of the computer program, may be provided for carrying out the determining and generating steps of the fourth aspect of the invention.

According to a fifth aspect of the present invention there is provided a method of correcting diamond Attenuated Total Reflectance (ATR) spectral data comprising the steps of:

receiving an initial set of ATR spectral data for a sample pressed into contact with a diamond ATR crystal;

numerically matching a pressure dependent diamond artefact reference spectrum to a corresponding pressure dependent diamond artefact in the initial set of ATR spectral data; and numerically subtracting out the numerically matched pressure dependent diamond artefact reference spectrum from the initial set of ATR spectral data to yield a corrected set of ATR spectral data for the sample.

According to a sixth aspect of the present invention there is provided a computer for correcting diamond Attenuated Total Reflectance (ATR) spectral data arranged under the control of software to:

receive an initial set of ATR spectral data for a sample pressed into contact with a diamond ATR crystal;

numerically match a pressure dependent diamond artefact reference spectrum to a corresponding pressure dependent diamond artefact in the initial set of ATR spectral data; and numerically subtract out the numerically matched pressure dependent diamond artefact reference spectrum from the initial set of ATR spectral data to yield a corrected set of ATR spectral data for the sample.

According to a seventh aspect of the present invention there is provided a computer program comprising code portions which when loaded and run on a computer cause the computer to carry out the steps of the fifth aspect of the invention.

Most if not all of the optional features described following the first, second and third aspects of the invention are equally applicable as optional features of the fifth, sixth and seventh aspect of the invention.

BRIEF DESCRIPTION OF THE DRAWINGS

Embodiments of the present invention will now be described, by way of example only, with reference to the accompanying drawings, in which.

DETAILED DESCRIPTION

Figure 1:
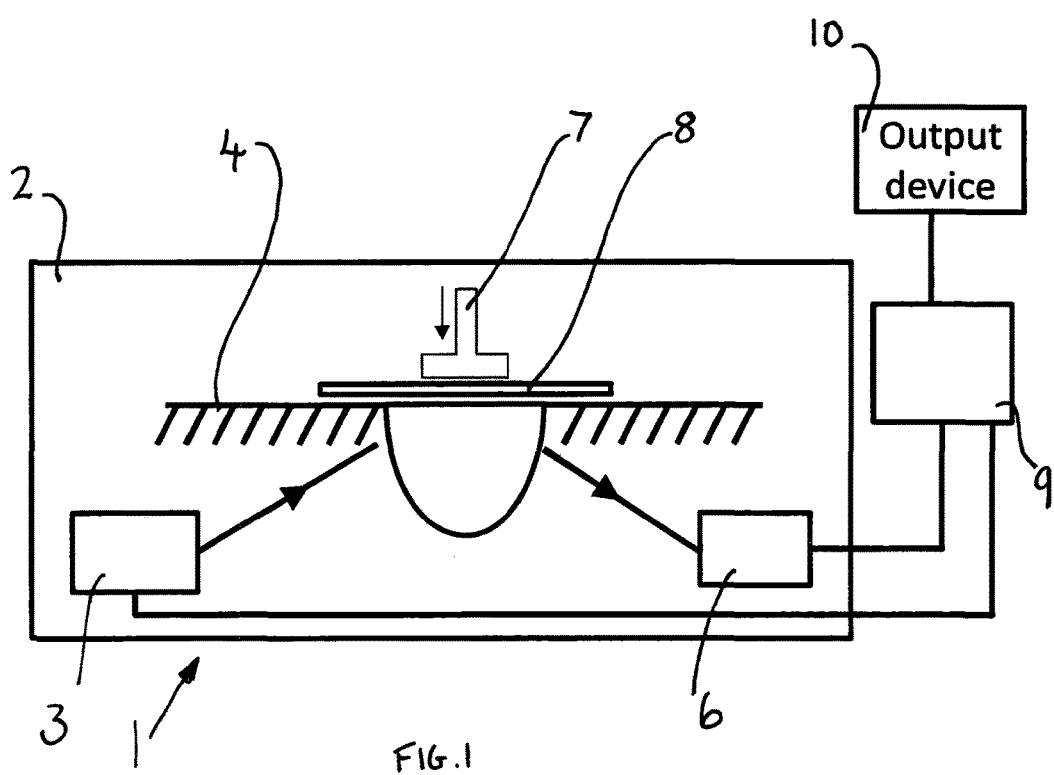
FIG. 1 schematically shows a spectrometer arranged for performing ATR measurements.

FIG. 1 shows, in highly schematic form, a spectrometer 1 arranged for performing Attenuated Total Reflectance (ATR) measurements and more particularly arranged under the control of software for producing corrected diamond ATR spectral data.

The spectrometer 1 comprises a main body 2 on which is mounted a source of radiation 3, a sample support surface 4 carrying an ATR crystal 5 and a detector 6. Also provided is a pressure applying means or clamp 7 for pressing a sample 8 into contact with the ATR crystal 5. Note that all of these components are shown only in highly schematic form in FIG. 1. The more detailed form of these aspects of ATR spectrometers is well known to those skilled in the art and not of particular relevance to the present invention. The spectrometer 1 also comprises a processing unit 9 with an associated output device 10. In the present embodiment the processing unit 9 and output device 10 are provided outside the main body 2 of the spectrometer 1 but in other embodiments these components may be provided integrally with the main body. Thus the processing unit 9 might be a general purpose computer connected to the remainder of the spectrometer 2 or might be an integral part of the main body of the spectrometer 2.

The processing unit 9 is connected to the source of radiation 3 to enable control of the source and connected to the detector 6 such that the output of the detector 6 can be fed to the processing unit 9 for processing. As is the case in all conventional ATR based spectrometers, radiation is directed to the ATR crystal 5, internally reflected at a facet of the crystal which is in contact with the sample 8 and progresses on to the detector 6. At the detector 6, the radiation as modified by its interaction with the sample during the total internal reflection process is detected and the resulting data is fed to the processing unit 9 to form an appropriate set of ATR spectral data.

As alluded to above, to this degree, the functioning of the current spectrometer is standard and thus more detailed description of its structure, function and operation is omitted for the sake of brevity. The present techniques may be used in respect of many different types of implementations of the structure and optical parts of the spectrometer. Thus these details are not of particular interest in the present application. What is of interest are the techniques used to allow for the fact that the diamond ATR crystal 5 introduces errors or artefacts into the spectral data measured using the spectrometer 1 due to the pressure dependent absorption features exhibited by diamond as mentioned in the introduction. In the present techniques, the processing unit 9 is arranged to operate on the spectral data as initially received from the detector 6.

In general terms the processing unit 9 is arranged under the control of software for carrying out various of the steps mentioned in more detail below which form part of the diamond ATR correction methods of the present application.

Figure 2:
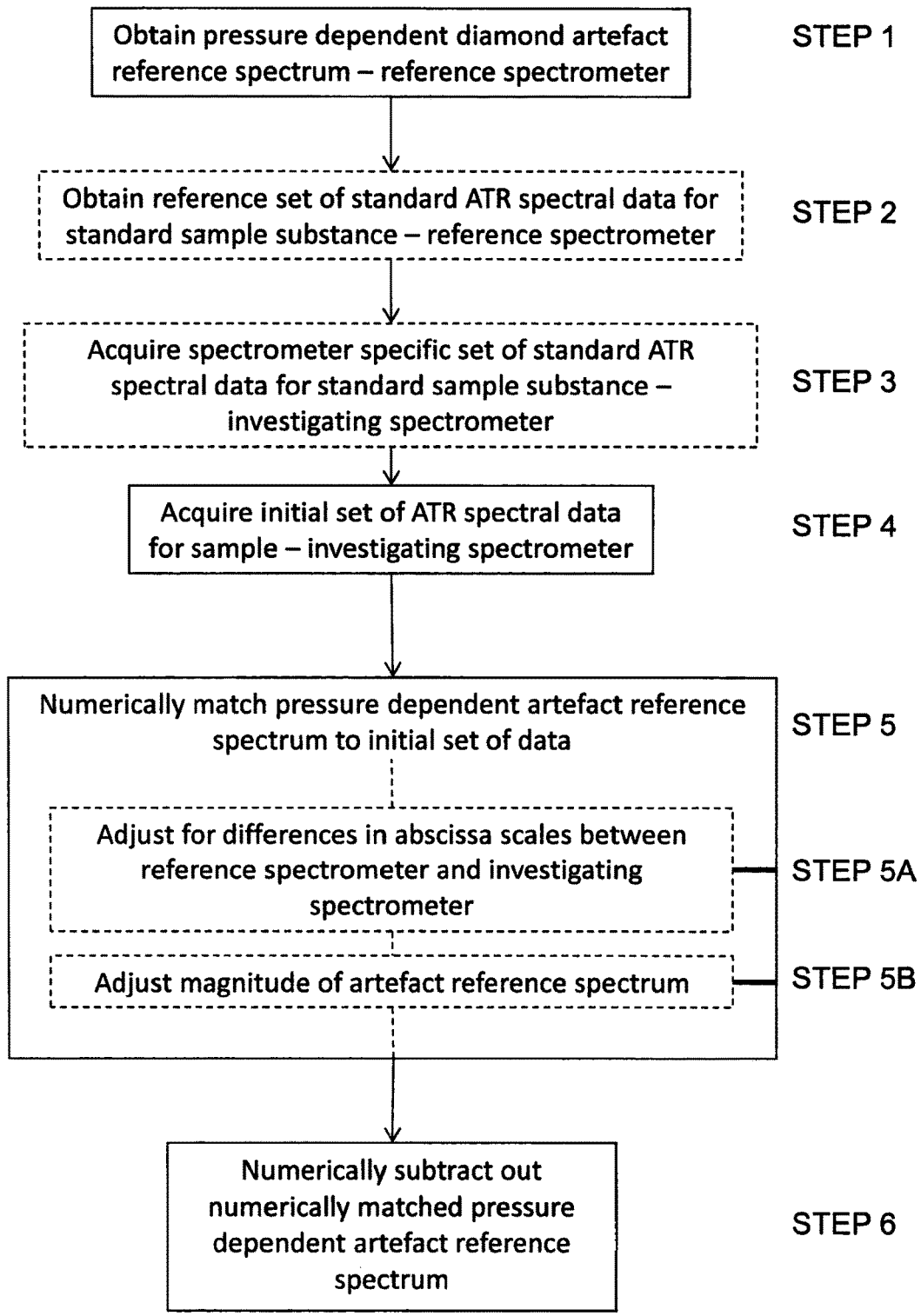
FIG. 2 is a flow chart showing an overview of a method for correcting ATR spectral data.

FIG. 2 shows, at a general level, a method for correcting sets of diamond ATR spectral data to remove the effect of pressure dependent diamond artefacts. The artefacts having been caused by the pressure exerted by the pressure applying means 7 through the sample 8 and onto the ATR crystal 5 during measurement of the diamond ATR spectra of the respective sample 8.

At the most generalised level, the method of FIG. 2 comprises obtaining a pressure dependent diamond artefact reference spectrum, acquiring an initial set of ATR spectral data for a sample, numerically matching the pressure dependent artefact reference spectrum to the corresponding features in the initial set of spectral data due to the diamond artefact and numerically subtracting out the numerically matched pressure dependent artefact spectrum.

Note that this technique does not require a measurement or assessment of the actual pressure being applied to the ATR crystal via the sample when the initial set of spectral data is acquired. Rather the numerical matching process is used to obviate the need for such a measurement or assessment. Thus this means that the present techniques are much more practical than ones where it would be necessary to attempt to measure or assess that applied pressure.

The process of FIG. 2 will now be described in more detail.

In step 1 the pressure dependent diamond artefact reference spectrum is obtained using a reference spectrometer. Typically this step will only be performed once by the manufacturer to develop the pressure dependent diamond artefact reference spectrum that then can be used in correcting spectral data for specific samples acquired using individual investigating spectrometers.

In the method of FIG. 2, in step 2 there is the optional step of obtaining a reference set of standard ATR spectral data for a standard sample substance. This is again acquired using the reference spectrometer. In effect this is a background measurement which can be useful in subsequent processing. Thus again this is a step which in general terms will be performed only once and most likely by the manufacturer. The pressure dependent diamond artefact spectrum of step 1 and the set of standard ATR spectral data for a standard sample substance of step 2 would then typically be supplied along with each new spectrometer (or indeed to users of existing spectrometers). Specifically this data might be stored in memory which is part of the processing unit 9 or provided separately on some storage media which may be accessed by the processing unit 9.

In step 3 an investigating spectrometer—i.e. the spectrometer of a user—is optionally used to acquire a spectrometer specific set of standard ATR spectral data for the standard sample substance. This is in effect taking the same background measurement of step 2 but on the user spectrometer whereas step 2 relates to taking that background spectrum on the reference spectrometer.

In step 4, an initial set of ATR spectral data for a sample of interest is acquired using the investigating spectrometer. If the present correction techniques were not to be used then this initial set of spectral data would be the output of the spectrometer. However in the present techniques we then move to step 5 of numerically matching the pressure dependent artefact reference spectrum as obtained in step 1 to the initial set of spectral data as obtained in step 4.

Once this numerical matching has occurred in step 5, then in step 6 the numerically matched pressure dependent diamond artefact reference spectrum may be subtracted out the initial set of ATR spectral data to yield a modified set of ATR spectral data for the sample which can be output by the output device 10. This may, for example, be a screen to display data to a user, or data output for further processing. Of course ultimately this ATR data can be used in determining the substance(s) present in the sample.

In the present embodiment, as shown in FIG. 2, the numerical matching step of step 5 may be broken down into two sub steps. First there is substep 5A which includes adjusting for differences in abscissa scales between the reference spectrometer and the investigating spectrometer and second there is substep 5B of adjusting the magnitude of the artefact reference spectrum to best fit the features as present in the initial set of ATR spectral data for the sample.

Thus, in effect step 5A is making an adjustment to shift the pressure dependent artefact reference spectrum in terms of wave number (or wave length, frequency etc) to, for example, allow for any abscissa calibration difference between the reference spectrometer and the investigating spectrometer so that the artefact reference spectrum "lines up" with the appropriate features in the initial set of data. On the other hand step 5B is useful to take account of the fact that the pressure applied by the pressure applying means 7 to the ATR crystal 5 can be different. It has been found that the pressure dependent artefact reference spectrum has a magnitude which is dependent on the applied pressure. Thus by adjusting the magnitude of the artefact reference spectrum numerically it is possible to find a magnitude which best fits the artefact as present in the initial set of ATR spectral data and thus numerically match the artefact reference spectrum to the initial set of data.

Note that the numerically matching steps of step 5 as shown in FIG. 2, are carried out using absorbance spectra as it eases calculations to work in a domain that is additive. In contrast the actual subtracting out step carried out in step 6 in FIG. 2 is carried out in transmittance to avoid losing the effect of any negative transmittance values.

Whilst the step of obtaining the pressure dependent diamond artefact reference spectrum using a reference spectrometer as shown in step 1 of FIG. 2 needs to be carried out, in principle, only once, it is important that a good clean pressure dependent diamond artefact reference spectrum is available for use in the numerical matching and numerical subtracting out steps.

Figure 3:
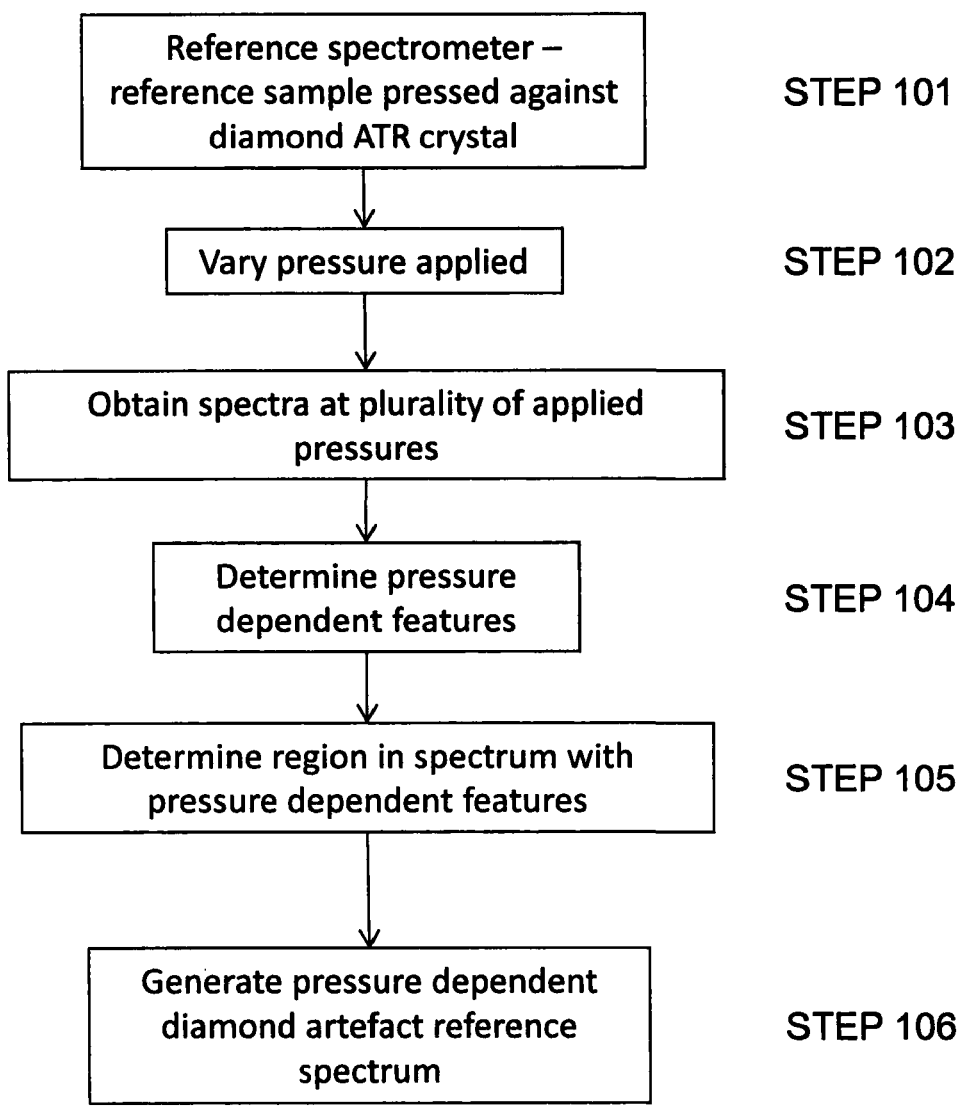
FIG. 3 is a flow chart showing an overview of more detail of the step of obtaining a pressure dependent diamond artefact reference spectrum as included in the method of FIG. 2.

FIG. 3 is a flow chart showing an overview of more detail of a process which may be used to obtain the pressure dependent diamond artefact reference spectrum which is the subject of step 1 in FIG. 2.

In the present technique for obtaining such a reference spectrum, then in step 101 a reference sample is pressed against the diamond ATR crystal. It will be appreciated that in obtaining such a reference spectrum, the same type of setup as shown in FIG. 1 may be used. However the reference sample should be carefully chosen. This should to be spectrally featureless in the range of interest. One possibility is to use a reflective material such as aluminium foil and another possibility would be to use an optically transparent reference sample such as $CaF_2$.

In step 102, the pressure applied to the ATR crystal via the sample is varied and in step 103 ATR spectra for the reference sample are obtained at a plurality of applied pressures.

In step 104 pressure dependent features in the obtained spectra are determined. This may be carried out, for example, by a principal component analysis. Alternatively, if, in the reference setup, it is possible to independently determine the applied pressure, other techniques such as partial least squares or principal component regression may be used.

In step 105, at least one region in the spectrum with pressure dependent features is determined. It is useful to limit the range of the pressure dependent artefact reference spectrum for use in the method of FIG. 2 to only that region or those regions where there is significant pressure dependence. This helps avoid a situation where corrections are being made using the reference spectrum which have a tendency to make the resulting data less accurate rather than more accurate. That is to say it reduces the risk of removing real features from the initial set of ATR spectral data.

In step 106 the pressure dependent artefact reference spectrum is generated taking into account the results of step 104 and step 105. As part of this process it should be ensured that the ends of the spectrum tend to zero such that the removal of the spectrum during step 6 of the method shown in FIG. 2 does not lead to steps in the finally determined output data. Thus the ends of the spectrum, or the ends of the different regions of spectrum if so determined, should be adjusted so as to slope to a zero offset.

Whilst the overall process of FIG. 2 is of interest and, as mentioned above, the obtaining of a good clean pressure dependent diamond artefact reference spectrum is important, more key parts of the present methods and apparatus are the numerical matching and numerical subtracting processes.

In some embodiments of the invention, all of the spectra determined in steps 1 and 4 of FIG. 2 may already be available and provided to the processing unit and the invention may reside in providing a corrected set of spectral data making use of these initial spectra. Thus in some embodiments the present invention may be embodied in a computer programmed to carry out the numerical matching and numerical subtracting out steps or similarly in a computer program comprising code portions which when executed on a computer, cause the computer to carry out the numerical matching and subtracting out steps to yield a corrected set of ATR spectral data for the sample.

Similarly the invention may be embodied in a spectrometer which can acquire the spectra of step 4 of FIG. 2 and (optionally) that of step 3 and arranged to carry out the numerical matching and numerical subtracting out steps.

Figure 4A:
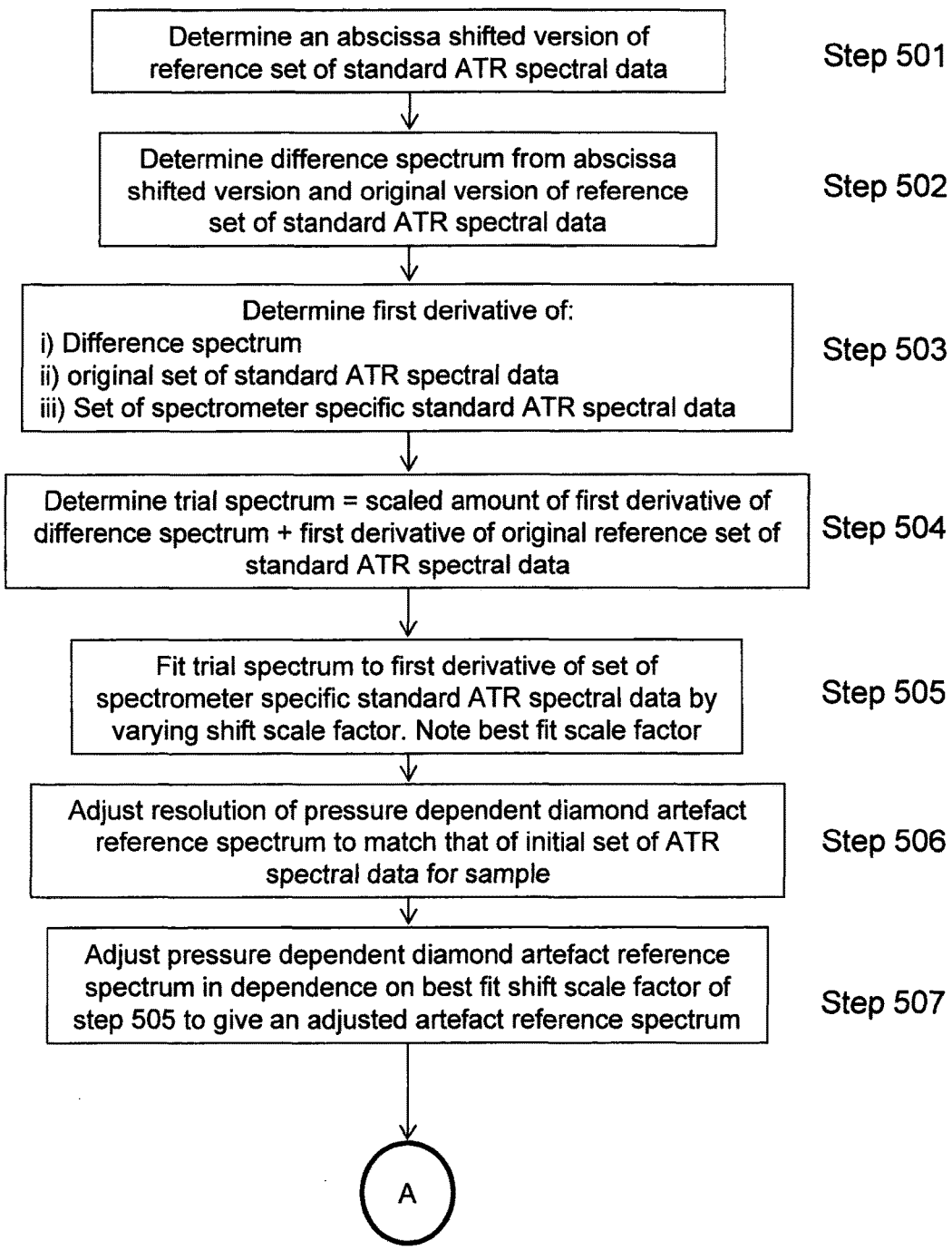
FIGS. 4A-4C is a flow chart giving an overview of more detail of the step of numerically matching the pressure dependent artefact reference spectrum to initial set of data as part of the overall method shown in FIG. 2.
Figure 4B:
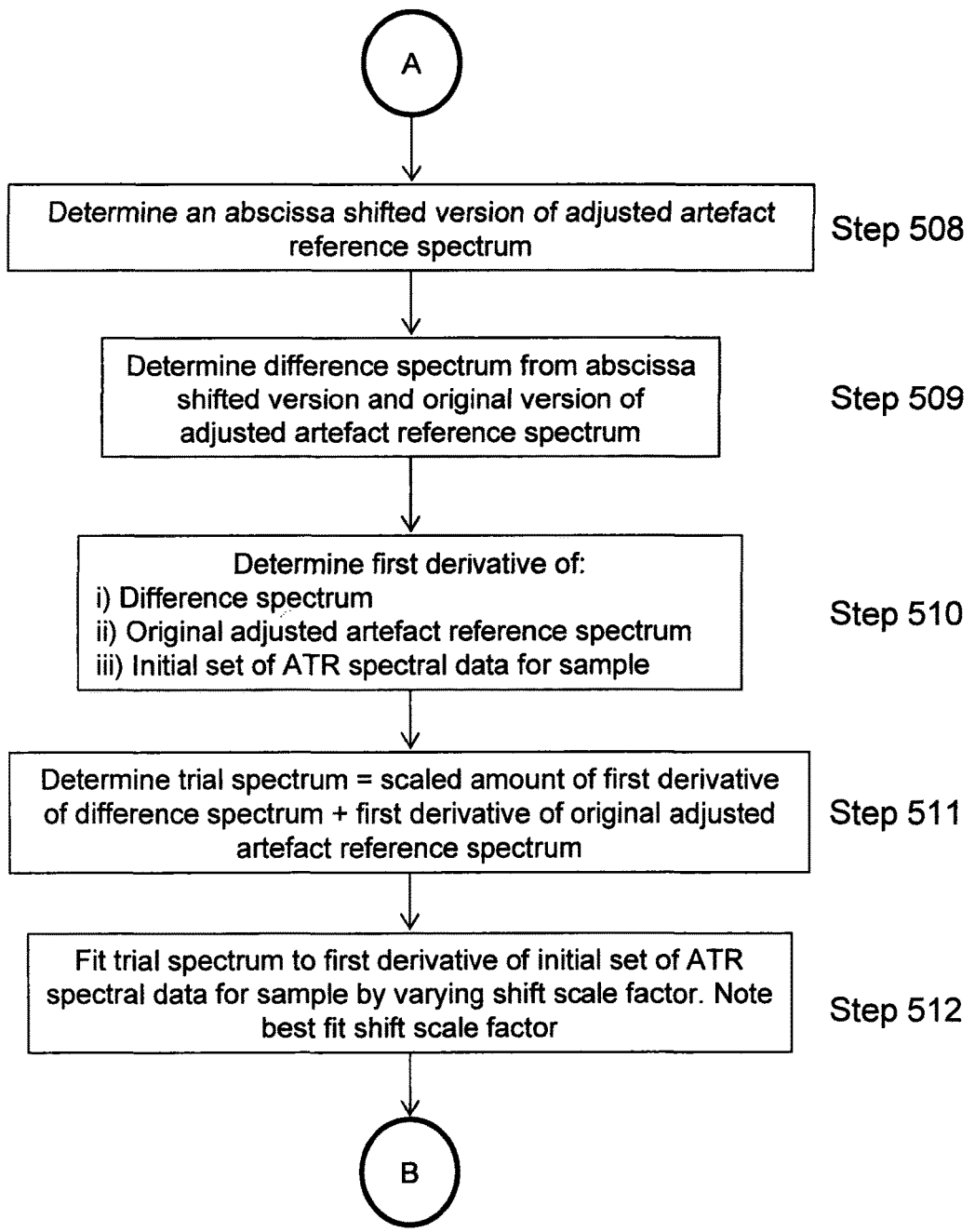
Figure 4C:
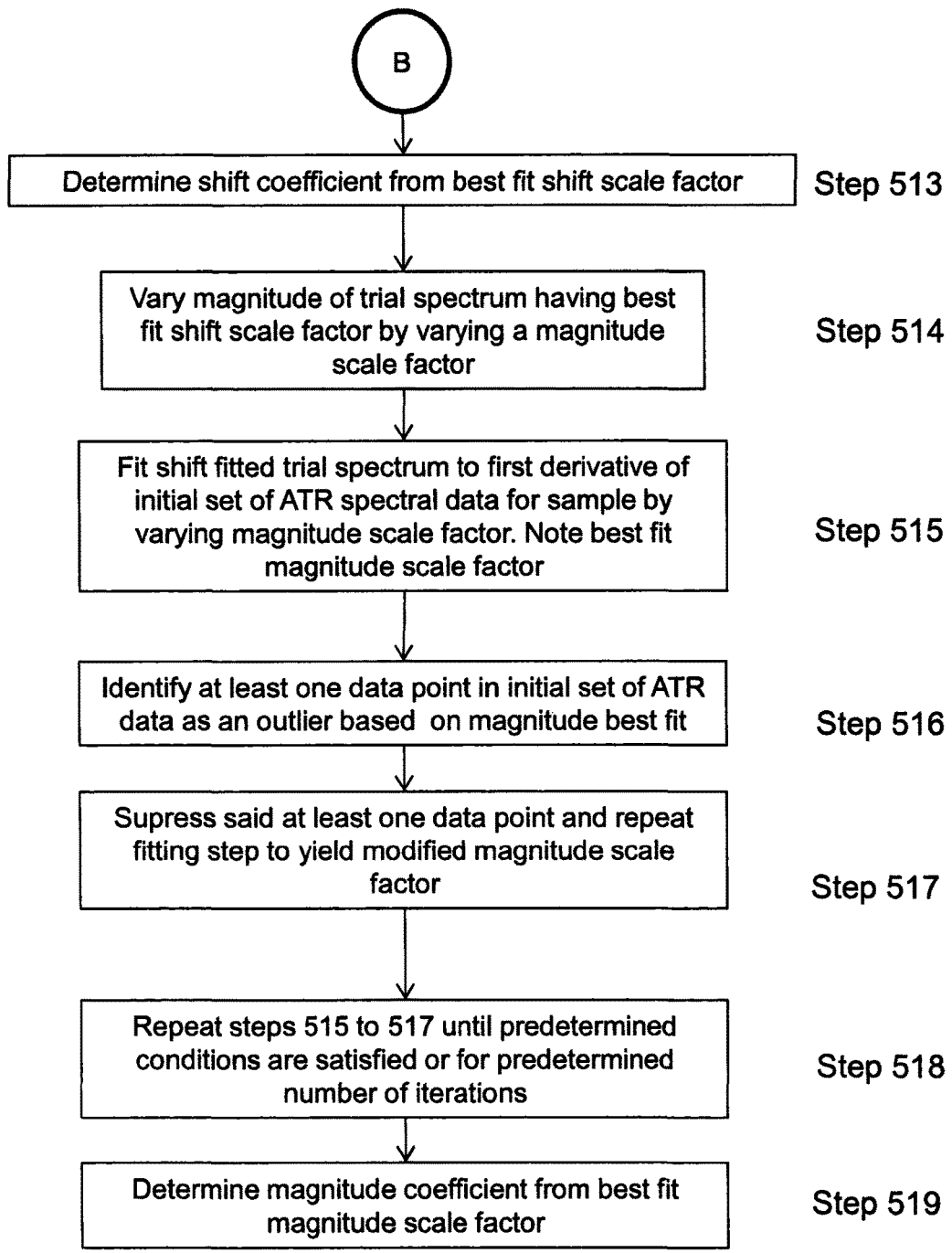
Figure 5:
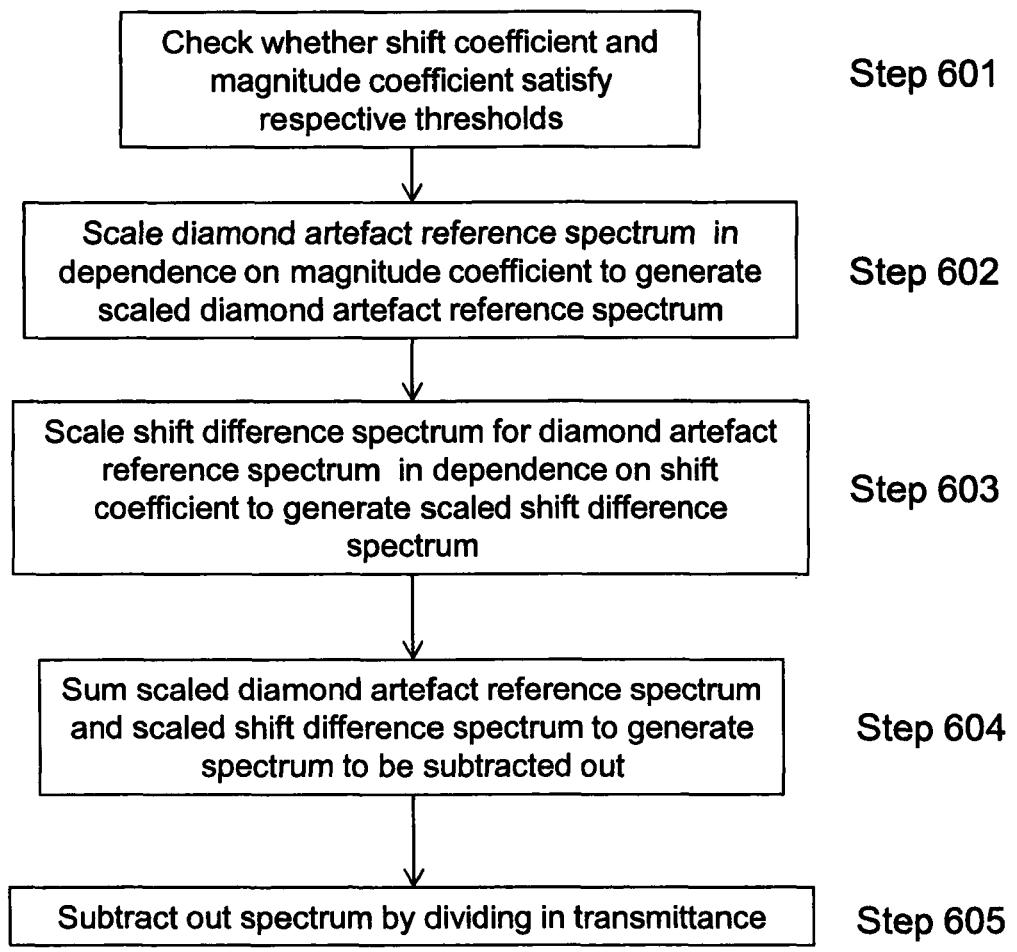
FIG. 5 is a flow chart showing an overview of more detail of the step of numerically subtracting out the numerically matched pressure dependent artefact spectrum step as included as part of the method of FIG. 2.

With this in mind, the numerical matching steps and numerical subtracting out steps of the overall process shown in FIG. 2 will be described in more detail below with reference to FIGS. 4 and 5. Note however that what is shown in and described with reference to FIGS. 3, 4 and 5 represent specific embodiments of the invention. Thus it should be remembered that not all of the steps referred to therein are essential for carrying out the invention. Various different alternatives may be chosen whilst still following the more fundamental basis of the present technique of starting with at least an initial set of ATR spectral data and a pressure dependent diamond artefact reference spectrum and then numerically matching the pressure dependent artefact reference spectrum to the initial set of data and following this numerically subtracting out the matched artefact spectrum from the spectral data to yield a modified set of spectral data.

As mentioned above in respect of FIG. 2, the numerical matching step 5 may be considered to have two substeps—step 5A and step 5B—relating to adjusting for differences in abscissa scales and adjusting for differences in magnitude.

Further, step 5A of adjusting for differences in abscissa scales may again be broken down into two distinct processes. The first is adjusting for differences in abscissa scales using background or standard sample substance data and the second is adjusting for abscissa scale differences using the pressure dependent diamond artefact features. In the embodiment shown in and described below in relation to FIG. 4, both of these types of abscissa scale correction are used. However this is not essential. It would be possible to use one or other of these. However using both of these types of abscissa scale correction is useful. By first adjusting for abscissa scale calibration differences using the background data, the risk of false correlations can be minimised. The abscissa matching process can then be fine tuned by making reference to the pressure dependent artefact features.

At a general level the process shown in FIG. 4 can be summarised in the following steps. First of all, adjustments for differences in abscissa scales, are made using the background data. After this the artefact reference spectrum is adjusted for resolution and to take into account the difference in abscissa scales. Following this, a further fine tune adjustment for differences in abscissa scales is made by considering the pressure dependent diamond artefact features. After this the magnitude of the adjusted pressure dependent diamond artefact reference spectrum is varied to find a best fit for magnitude. The end of this process yields a shift coefficient relating to the differences in abscissa scales and a magnitude coefficient relating to the size of the pressure dependent diamond artefact in the sample data.

With this summary in mind the process as illustrated in FIG. 4 will be described in more detail below.

In step 501 an abscissa shifted version of the reference set of standard ATR spectral data is determined. It will be recalled that this reference set of standard ATR spectral data is in effect a background reading taken on the original reference spectrometer used to develop the pressure dependent diamond artefact reference spectrum.

In step 502 a difference spectrum is determined from the abscissa shifted version of the reference set of ATR spectral data as determined in step 501 and the original version of the reference set of standard ATR spectral data.

In step 503 first derivatives are determined of the difference spectrum, the original set of standard ATR spectral data and the set of spectrometer specific standard ATR spectral data. Thus at this stage one has first derivatives of the difference spectrum, the background spectrum on the reference spectrometer and the background spectrum on the investigating spectrometer.

In step 504 a trial spectrum is determined. This consists of a scaled amount of the first derivative of the difference spectrum summed with the first derivative of the original reference set of standard ATR spectral data.

In step 505 the trial spectrum of step 504 is fitted to the first derivative of the set of spectrometer specific standard ATR spectral data by varying the shift scale factor. Thus at this stage there is the operation of fitting the background spectrum taken on the reference spectrometer to the background spectrum taken on the investigating spectrometer with the actual fit being carried out using first derivatives to filter out slowly varying/baseline features. Out of the end of this process a best fit scale factor is determined which is representative of the difference in abscissa calibration between the reference spectrometer and the investigating spectrometer.

Next in step 506 a process of fitting the pressure dependent diamond artefact reference spectrum is begun. The first step as included in step 506 is adjusting the resolution of the pressure dependent artefact reference spectrum to match that of the initial set of ATR spectral data acquired for the sample (as was acquired for example in step 4 of the process shown in FIG. 2).

In step 507, the pressure dependent diamond artefact reference spectrum is operated on in dependence on the best fit shift scale factor found in step 505 so that the effect of the differences in abscissa calibration can be taken into account. This yields an adjusted artefact reference spectrum which has been shifted in terms of abscissa position. As a result of this, the abscissa position of the adjusted artefact reference spectrum should be close to where the corresponding diamond artefact features should be present in the initial set of ATR spectral data for the sample.

Next in steps beginning with step 508, a process of more finely adjusting the abscissa position of the reference spectrum is undertaken by fitting the adjusted artefact reference spectrum to the initial set of ATR spectral data for the sample in terms of abscissa position. The steps used in this part of the process, namely steps 508-512 are to a large degree a repetition of steps 502-505 described above but are carried out in respect of the spectra including the pressure dependent diamond artefact features rather than the background spectra.

Thus in step 508 an abscissa shifted version of the adjusted artefact reference spectrum is determined. In step 509 a difference spectrum is determined from the abscissa shifted version of the adjusted artefact reference spectrum and the original adjusted artefact reference spectrum.

In step 510 first derivatives are determined of the difference spectrum found in step 509, the original adjusted artefact reference spectrum as found in 507 and the initial set of ATR spectral data for a sample as found for example in step 4 of the process shown in FIG. 2.

In step 511 a trial spectrum is determined. This is made up of a scaled amount of the first derivative of the difference spectrum summed with a first derivative of the original adjusted artefact reference spectrum.

Then in step 512 the trial spectrum is fitted to the first derivative of the initial set of ATR spectral data for the sample by varying the shift scale factor. The best fit shift scale factor is then noted.

In step 513 a shift coefficient for shifting the adjusted artefact reference spectrum by an amount which should most closely fit the reference artefact spectrum to the corresponding artefact features in the sample data is determined from the best fit shift scale factor. Thus by the completion of step 513 an optimum abscissa position for the artefact reference spectrum has been determined.

Next in steps 514-519 a sub process of fitting the artefact reference spectrum to the sample data in terms of magnitude is carried out.

This sub process starts in step 514 by taking the trial spectrum of step 511 whilst using the best fit shift scale factor and varying the magnitude of the trial spectrum. Then in step 515 the shift fitted trial spectrum is fitted to the first derivative of the initial set of ATR spectral data for the sample by varying the magnitude scale factor. The best fit magnitude scale factor is then noted.

However at this stage it is appreciated that real features in the data might be skewing the best fit magnitude value. Therefore in step 516 at least one data point in the initial set of ATR data is identified as an outlier in the magnitude best fit.

After this in step 517 the at least one data point is suppressed and the fitting step of 515 is repeated with that data point suppressed to yield a modified best fit magnitude scale factor. An improved best fit scale factor should thereby be obtained.

In steps 518, steps 515-517 may be repeated until predetermined conditions are satisfied or for predetermined number of iterations with new outlier data points being determined and suppressed in each iteration. This should improve the fit. In one specific example the process may be repeated three times. In another implementation the process might be repeated until the magnitude scale factor stabilises, that is to say, until the variation of magnitude scale factor between one iteration and the next is below some threshold value, for example.

In step 519 a magnitude coefficient is determined from the best fit magnitude scale factor.

The shift coefficient determined in step 513 and magnitude coefficient determined in step 519 are then available for use in determining the best abscissa position and magnitude for the adjusted artefact reference spectrum to facilitate its removal from the sample data.

The process of numerically subtracting out the numerically matched pressure dependent artefact spectrum, making use of the shift coefficients and magnitude coefficients determined by the process shown in FIG. 4, is illustrated in more detail in FIG. 5.

In step 601 the reasonableness of the shift coefficient and magnitude coefficient is checked. In particular the shift coefficient and magnitude coefficient are checked against respective thresholds. Thus, for example, a maximum plausible value for the shift coefficient and the magnitude coefficient may be determined based on the biggest shift which could be expected and the largest artefact features which could be expected under the maximum pressure exertable in any typical ATR spectrometer. These maximum values could then be used as upper thresholds for the coefficient.

In step 602 the diamond artefact reference spectrum is scaled in dependence on the magnitude coefficient to generate a scaled diamond artefact reference spectrum.

In step 603 a shifted difference spectrum for the diamond artefact reference spectrum is determined in dependence on the shift coefficient. In fact this means determining an abscissa shifted version of the artefact reference spectrum, determining a difference spectrum from the abscissa shifted and original versions of the diamond artefact reference spectrum to yield the shift different spectrum. This shift difference spectrum can then be scaled in dependence on the shift coefficient.

In step 604 the scaled diamond artefact reference spectrum and scaled shift difference spectrum can be summed to generate the spectrum to the subtracted out.

This spectrum is then converted back to transmittance so that it may be subtracted out of the sample data (also in transmittance) by dividing the spectra. This avoids losing any negative terms.

Figure 6A:
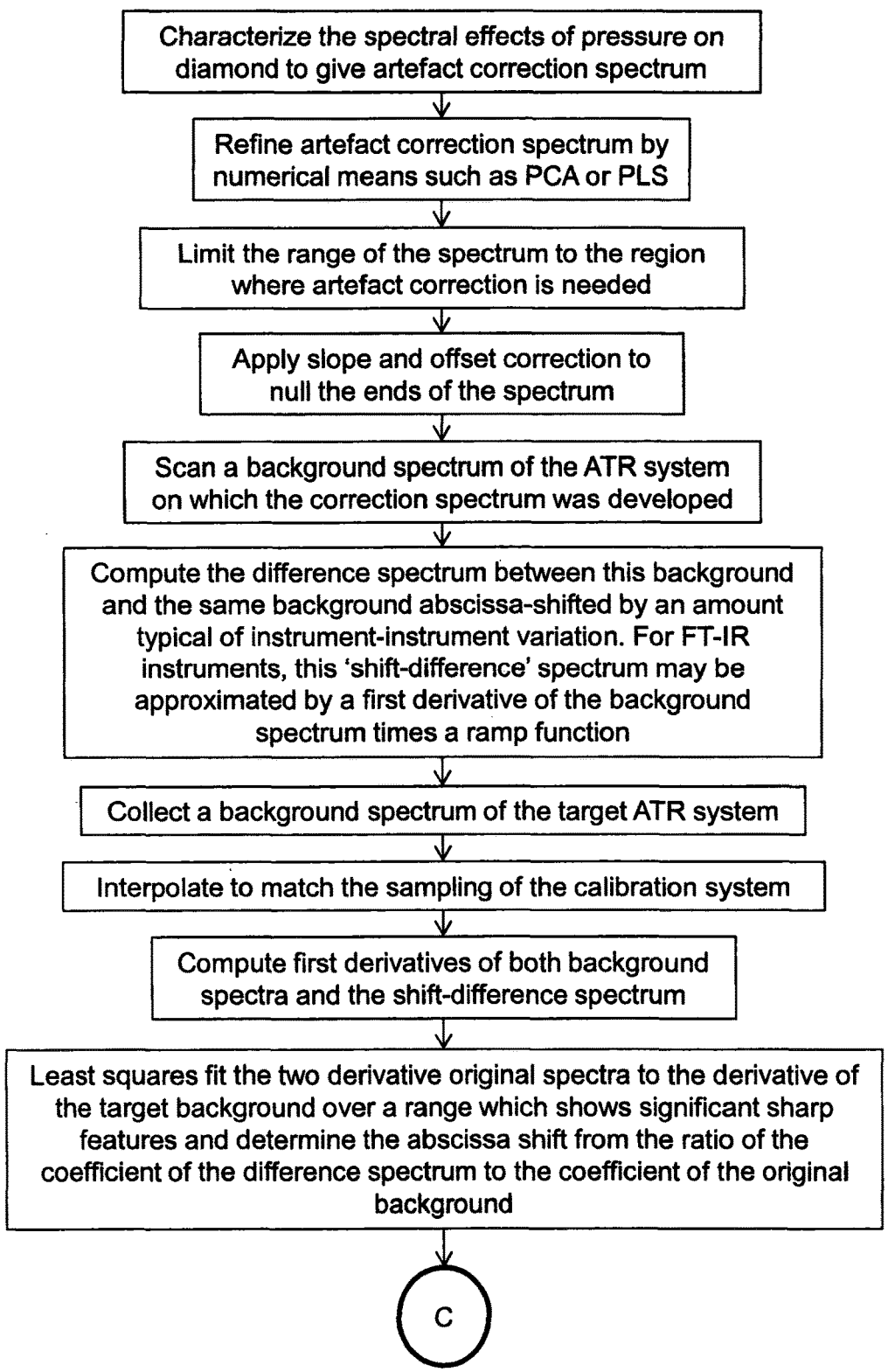
FIGS. 6A-6B is a flow chart giving more detail of a particular implementation of the method of correcting diamond ATR spectral data as shown in FIG. 2.
Figure 6B:
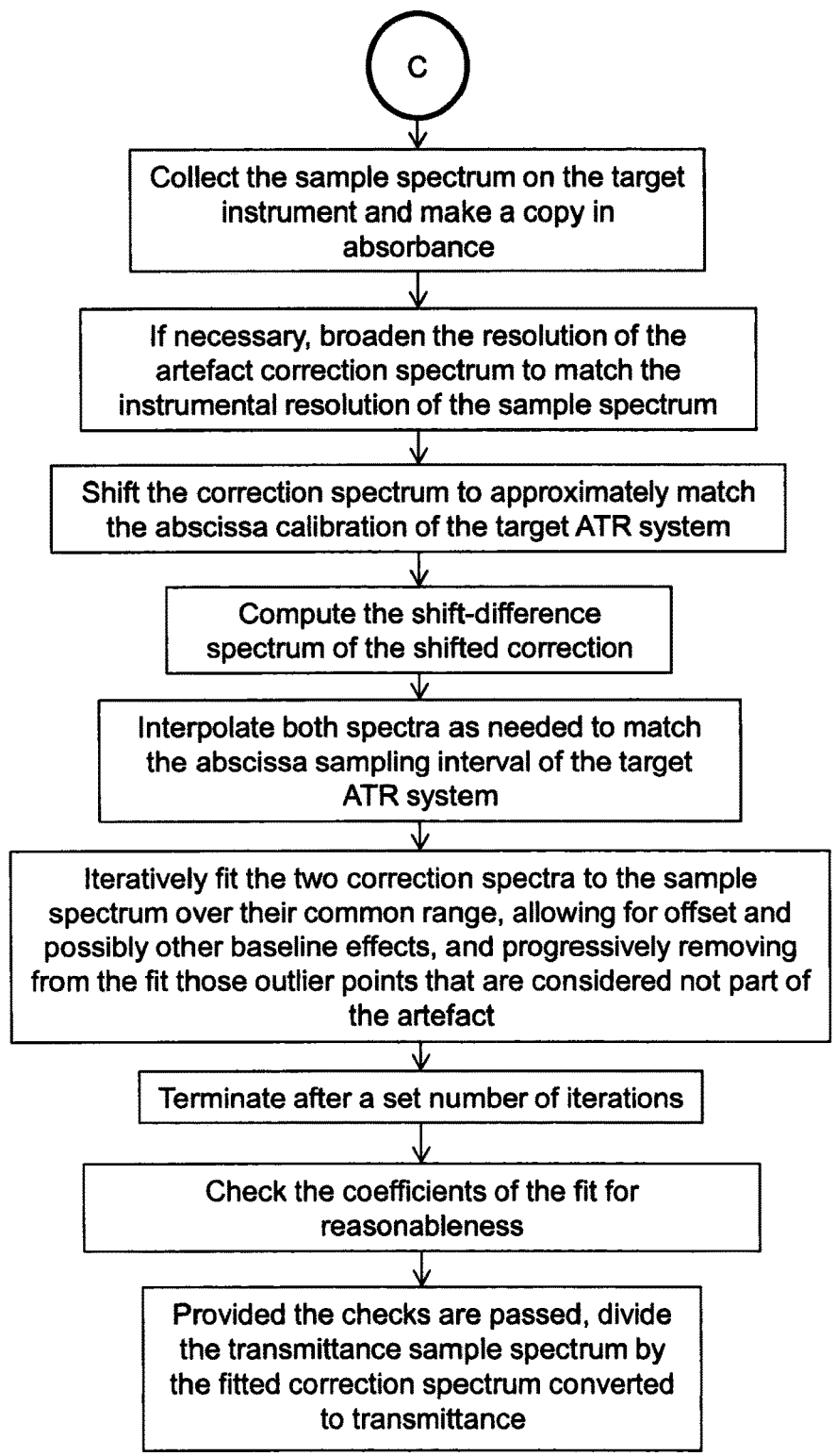

FIG. 6 is a flow chart showing in more detail one example of carrying out the whole process indicated in FIG. 2.

Below is a description of the matching and subtracting processes of steps 5 and 6 of FIG. 2 used in a specific example where it is desired to correct an ATR spectrum for a polyethylene sample.

Figure 7:
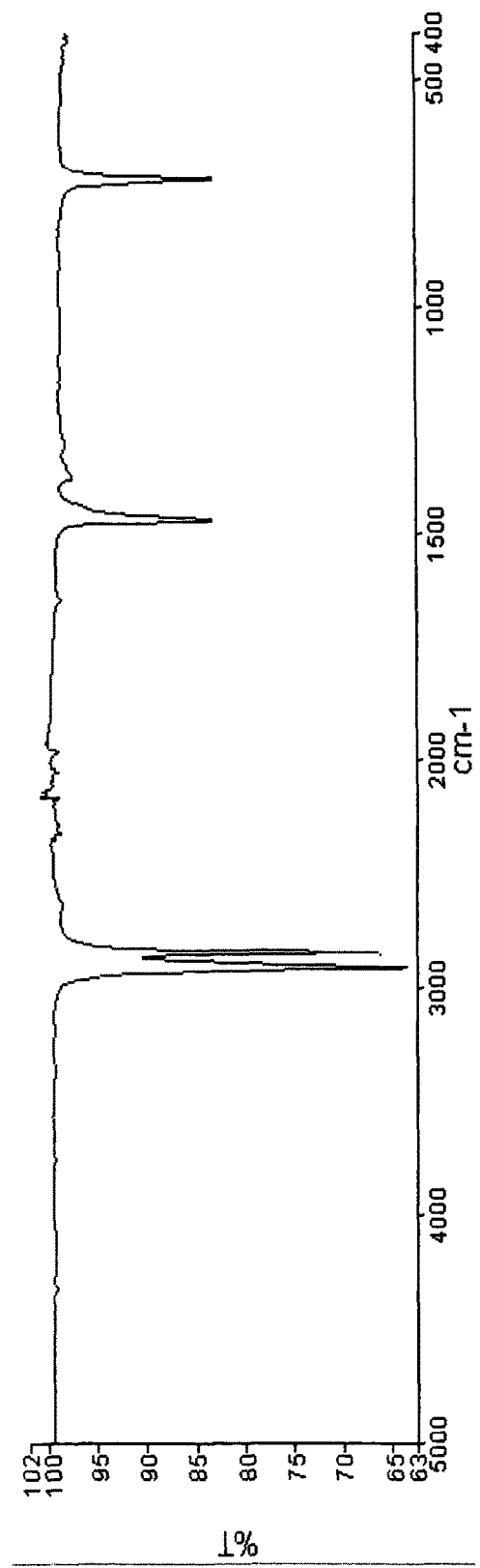
FIG. 7 is a plot showing an uncorrected diamond ATR spectrum for polyethylene exhibiting pressure dependent diamond artefact features.

An example spectrum for polyethylene before correction is shown in FIG. 7. The region centred on 2000 cm$^{-1}$ should be quite featureless but shows clear evidence of the diamond ATR pressure dependent artefact.

The series of steps described below start from a position where, from the reference (or calibration) spectrometer, we have available the pressure dependent diamond artefact reference spectrum (or restricted range ATR artefact spectrum/correction spectrum) and the reference set of standard ATR spectral data for a standard sample substance (the reference ATR background). Further we have available the initial set of spectral data for a sample (the uncorrected sample spectrum) and a spectrometer specific set of standard ATR spectral data for the standard sample substance (the target ATR background).

Note that the terminology used in the example below is in some instances different from that used above in the description of FIGS. 1-5 but how the steps correspond to those described above should be clear. More detail of the precise steps taken is given for this example than in the more generalised method described above. The steps taken in the example are:

a) truncate the range of the calibration background to a suitable region of strong sharp features, in this case 2180-1994 cm$^{-1}$; convert the spectrum to log (quasi-absorbance).

b) interpolate and truncate the target background to match the calibration background sampling; convert to log.

c) compute the centered difference (essentially the first derivative) of the calibration background and multiply by a ramp function proportional to wavenumber starting at 0.5 for the highest wavenumber in the range. This generates essentially a 'shift-difference' spectrum.

d) compute the adjacent differences (a simple first derivative) of all three spectra and truncate the ranges a little to avoid end effects.

e) least squares fit the derivative calibration spectra to the derivative target spectrum allowing for ordinate offset shift f) compute the fractional abscissa calibration difference from the ratio of the fit coefficient of the centered difference component and the fit coefficient of the calibration background component.

g) if necessary, broaden the artefact calibration (correction) spectrum to match the resolution of the target sample spectrum. Sufficient accuracy is achieved here with a convolution filter representing the approximate instrument line shape of the target instrument. However, conceptually the process can be substantially more complex.

h) interpolate and shift the correction spectrum to match the data interval and abscissa calibration as determined by steps a-f; convert to log.

i) similarly to step c, compute the centered difference times ramp of the correction spectrum to yield the shift-difference spectrum.

j) truncate the target spectrum to the range of the correction spectra and convert to log.

k) least squares fit the correction spectra to the target spectrum allowing for ordinate offset.

l) compute the rms fit residue (sigma)

m) rerun the least squares fit excluding points corresponding to outliers with residue outside +/−4 sigma n) recompute sigma excluding outliers o) iterate steps m and n a suitable number of times (we used 3)

p) check that the fit coefficients for the correction spectrum and the shift-difference spectrum are sensible. We set the scale of the correction spectrum to be the largest we could ever expect, meaning that its coefficient should never exceed 1. Equally, if the shift calibration performed in steps a-f is effective, the scale of the shift-difference coefficient should never exceed 1 in a realistic correction situation.

q) provided the fit coefficients are sensible, compute the scaled combination of correction and shift-difference spectra, take the antilog (convert to transmittance) and divide into the full range sample transmittance spectrum over the correction range.

Below are details of some more specific and optional details of the method as performed by the applicant in developing the present invention.

In developing the diamond artefact reference spectrum spectral resolution of 2 cm$^{-1}$ might typically be used.

In limiting the range of, or trimming the artefact reference spectrum, then it may be appropriate to set the limits on the range of the spectrum to 2700-1800 cm$^{-1}$.

Note that when adjusting for differences in abscissa scales between the reference and investigating (target) instrument, multipoint abscissa calibration is needed for dispersive spectrometers. On the other hand for Fourier Transform (FT) instruments, for example, a single scale factor should be adequate.

When producing a background or standard sample spectrum, then whilst above the diamond ATR substrate itself is used as the standard sample substance, it would be possible to use other substances. In particular, for example, a liquid such as toluene which requires no pressure to keep it in intimate contact with the ATR crystal might be used.

Further, whilst in the specific examples described above, first derivatives are used for preprocessing/filtering the data, other preprocessing might be used. For example different filters such as second derivatives or other filters may be used, as might baseline subtraction.

As part of the abscissa matching process, the shift difference spectrums mentioned above might be determined as an approximation by the use of a first derivative times a linear ramp function which is proportional to wave number.

In step 506 described in relation to FIG. 4 above, the step of adjusting the resolution of the artefact reference spectrum is mentioned. As well as this it is possible to also interpolate to match the sampling interval between the spectrum and that of the investigating (or target) instruments/spectrometer. Further a convolution filter may be applied representing the difference in instrument line shapes between the reference spectrometer and investigating spectrometer. Further, optionally, cubic spline or higher order interpolation may be used.

When shifting the artefact spectrum to match the abscissa scale of the investigating spectrometer for FT instruments, it is appropriate to use the predetermined abscissa scaling factor whereas for dispersive spectrometers the multipoint abscissa calibration could be used. Further cubic spline or higher order interpolation may be used in conjunction with the scaled abscissa value to generate the shift.

When one is fitting the adjusted artefact spectrum to the sample spectrum in terms of magnitude, offset slope and other polynomial terms may be included in the fit to help in the fitting process.

It should also be noted that the step of shifting the artefact spectrum based on comparing the artefact reference spectrum to the position of the corresponding features in the sample data as outlined in steps 508-513 of FIG. 4 is optional. In some circumstances it may be determined or decided that it is sufficient to carry out abscissa calibration shift based only on the background/standard sample comparison as explained in steps 501-505 of FIG. 4.

The invention claimed is:

1. A method for investigating physical and/or chemical properties of a sample comprising the steps of:
   pressing a sample into contact with a diamond Attenuated Total Reflectance (ATR) crystal on a sample supporting surface of a spectrometer by a pressure applying means;
   directing radiation to an ATR crystal by a radiation source;
   the radiation modified by contact with the sample to produce modified radiation;
   detecting the modified radiation at a detector;
   acquiring, using the spectrometer, an initial set of ATR spectral data for the sample;
   numerically matching, using the spectrometer, a pressure dependent diamond artefact reference spectrum to a corresponding pressure dependent diamond artefact in the initial set of ATR spectral data; and
   numerically subtracting out the numerically matched pressure dependent diamond artefact reference spectrum from the initial set of ATR spectral data to yield a corrected set of ATR spectral data for the sample to determine physical and/or chemical properties of the sample without directly measuring a pressure applied to the crystal by the sample.

2. A method according to claim 1 in which the numerically matching step comprises adjusting the magnitude of the artefact reference spectrum.

3. A method according to claim 2 in which the step of adjusting the magnitude of the artefact reference spectrum comprises finding a magnitude that yields a best fit between the pressure dependent diamond artefact reference spectrum and the corresponding pressure dependent diamond artefact in the initial set of ATR spectral data.

4. A method according to claim 3 in which the step of adjusting the magnitude of the artefact reference spectrum comprises the steps of:
   i) finding a magnitude that yields a best fit between the pressure dependent diamond artefact reference spectrum and the corresponding pressure dependent diamond artefact in the initial set of ATR spectral data;
   ii) identifying at least one data point from the best fit as an outlier;
   iii) suppressing said at least one data point and finding a modified magnitude that yields a modified best fit between the pressure dependent diamond artefact reference spectrum and the corresponding pressure dependent diamond artefact in the initial set of ATR spectral data with said at least one data point suppressed.

5. A method according to claim 4 in which the identifying and the suppressing and the finding are iterated suppressing further data points in each iteration.

6. A method according to claim 1 in which the numerically matching step comprises adjusting for differences in abscissa scales associated with the reference spectrum and the initial set of spectral data.

7. A method according to claim 6 in which the step of adjusting for differences in abscissa scales comprises the step of:
   comparing a spectrometer specific standard ATR spectral data for a standard sample substance with a reference set of standard ATR spectral data for the standard sample substance.

8. A method according to claim 7 in which the standard sample substance is diamond.

9. A method according to claim 7 in which the step of adjusting for differences in abscissa scales comprises the steps of:
   first adjusting for differences in abscissa scales based on the comparison between the spectrometer specific standard ATR spectral data and the reference set of standard ATR spectral data for the standard sample substance; and
   after this further adjusting for differences in abscissa scales based on a comparison between the pressure dependent diamond artefact reference spectrum and the corresponding pressure dependent diamond artefact in the initial set of ATR spectral data.

10. A method according to claim 7 in which the step of adjusting for differences in abscissa scales comprises the steps of:
    determining an abscissa shifted version of the reference set of standard ATR spectral data;
    determining a difference spectrum from the difference between the abscissa shifted version of the reference set of standard ATR spectral data and the original reference set of standard ATR spectral data;
    determining a trial spectrum by adding a scaled amount of the difference spectrum to the original reference set of standard ATR spectral data, the scaled amount comprising a shift scale factor;
    fitting the trial spectrum to the set of spectrometer specific standard ATR spectral data by varying the shift scale factor to obtain the best fit; and
    determining an appropriate abscissa scale adjustment in dependence on the shift scale factor corresponding to the best fit.

11. A method according to claim 7 in which the step of adjusting for differences in abscissa scales comprises the steps of:
    determining an abscissa shifted version of the reference set of standard ATR spectral data;
    determining a difference spectrum from the difference between the abscissa shifted version of the reference set of standard ATR spectral data and the original reference set of standard ATR spectral data;
    determining the first derivative of the difference spectrum, the first derivative of the original reference set of standard ATR spectral data, and the first derivative of the set of spectrometer specific standard ATR spectral data;
    determining a trial spectrum by adding a scaled amount of the first derivative of the difference spectrum to the first derivative of the original reference set of standard ATR spectral data, the scaled amount comprising a shift scale factor;
    fitting the trial spectrum to the first derivative of the set of spectrometer specific standard ATR spectral data by varying the shift scale factor to obtain the best fit; and
    determining an appropriate abscissa scale adjustment in dependence on the shift scale factor corresponding to the best fit.

12. A method according to claim 11, in which the step of adjusting for differences in abscissa scales comprises the steps of:
    adjusting the pressure dependent diamond artefact reference spectrum in dependence on the determined abscissa scale adjustment to give an adjusted artefact reference spectrum;
    determining an abscissa shifted version of the adjusted artefact reference spectrum;

determining a difference spectrum from the difference between the abscissa shifted version of the adjusted artefact reference spectrum and the original adjusted artefact reference spectrum;

determining the first derivative of the difference spectrum, the first derivative of the original adjusted artefact reference spectrum, and the first derivative of the initial set of ATR spectral data;

determining a trial spectrum by adding a scaled amount of the first derivative of the difference spectrum to the first derivative of the original adjusted artefact reference spectrum, the scaled amount comprising a shift scale factor;

fitting the trial spectrum to the first derivative of the initial set of ATR spectral data by varying the shift scale factor to obtain the best fit; and determining a further appropriate abscissa scale adjustment in dependence on the shift scale factor corresponding to the best fit.

13. A method according to claim 1 in which the numerically matching step comprises pre-processing at least one of the sets of ATR spectral data and/or pre-processing the pressure dependent diamond artefact reference spectrum to suppress slow baseline variation.

14. A method according to claim 1 in which the numerically matching step comprises the step of adjusting the resolution of the diamond artefact reference spectrum to match the resolution of the initial set of ATR spectral data.

15. A method according to claim 1 wherein the numerically matching step comprises adjusting the magnitude of the artefact reference spectrum, wherein the step of adjusting the magnitude of the artefact reference spectrum includes the determination of at least one magnitude coefficient, the numerically matching step comprises adjusting for differences in abscissa scales associated with the reference spectrum and the initial set of spectral data, and the step of adjusting for differences in abscissa scales includes the determination of at least one shift coefficient and the method comprises checking whether the at least one magnitude coefficient satisfies at least one respective threshold and checking whether the at least one shift coefficient satisfies at least one respective threshold.

16. A method according to claim 1 in which the step of numerically subtracting out the numerically matched pressure dependent diamond artefact reference spectrum may comprise dividing in transmittance.

17. The method of claim 1 further comprising outputting the corrected set of ATR spectral data by an output device coupled to the spectrometer.

18. The method of claim 17 wherein the outputting by an output device comprises outputting to a screen for display to a user.

19. The method of claim 17 wherein the outputting by an output device comprises outputting data for further processing.

20. The method of claim 17 wherein the outputting comprises outputting data to determine a substance present in the sample.

21. A spectrometer arranged for performing Attenuated Total Reflectance (ATR) measurements comprising:
a source of radiation;
a detector for detecting radiation having passed through a diamond ATR crystal positioned in the spectrometer; and
a processing unit for processing the output of the detector to produce sets of ATR spectral data;

wherein the spectrometer has a memory for storing a pressure dependent diamond artefact reference spectrum and is arranged to acquire an initial set of ATR spectral data for a sample pressed into contact with a diamond ATR crystal;

and the processing unit is arranged to:
numerically match the pressure dependent diamond artefact reference spectrum to a corresponding pressure dependent diamond artefact in the initial set of ATR spectral data; and
numerically subtract out the numerically matched pressure dependent diamond artefact reference spectrum from the initial set of ATR spectral data to yield, without directly measuring a pressure applied to the crystal by the sample, a corrected set of ATR spectral data for the sample for output by the spectrometer to allow a determination of physical and/or chemical properties of the sample.

22. A method of producing corrected diamond Attenuated Total Reflectance (ATR) spectral data comprising the steps of:
obtaining a pressure dependent diamond artefact reference spectrum on a first reference spectrometer;
acquiring, using a second spectrometer, an initial set of ATR spectral data for a sample pressed into contact with a diamond ATR crystal;
numerically matching, using the second spectrometer, the pressure dependent diamond artefact reference spectrum to a corresponding pressure dependent diamond artefact in the initial set of ATR spectral data; and
numerically subtracting out the numerically matched pressure dependent diamond artefact reference spectrum from the initial set of ATR spectral data to yield, without directly measuring a pressure applied to the crystal by the sample, a corrected set of ATR spectral data for the sample for output by the spectrometer to allow a determination of physical and/or chemical properties of the sample.

23. A method of correcting diamond Attenuated Total Reflectance (ATR) spectral data comprising the steps of:
receiving an initial set of ATR spectral data for a sample pressed into contact with a diamond ATR crystal;
numerically matching a pressure dependent diamond artefact reference spectrum to a corresponding pressure dependent diamond artefact in the initial set of ATR spectral data; and
numerically subtracting out the numerically matched pressure dependent diamond artefact reference spectrum from the initial set of ATR spectral data to yield, without directly measuring a pressure applied to the crystal by the sample, a corrected set of ATR spectral data for the sample for output by a spectrometer to allow a determination of physical and/or chemical properties of the sample.

24. A non-transitory machine readable data carrier carrying a computer program comprising code portions which when loaded and run on a computer cause the computer to carry out the method of claim 23.

25. A computer for correcting diamond Attenuated Total Reflectance (ATR) spectral data arranged under the control of software to:
receive an initial set of ATR spectral data for a sample pressed into contact with a diamond ATR crystal;
numerically match a pressure dependent diamond artefact reference spectrum to a corresponding pressure dependent diamond artefact in the initial set of ATR spectral data; and numerically subtract out the numerically matched pressure dependent diamond artefact reference spectrum from the initial set of ATR spectral data to yield, without directly measuring a pressure applied to the crystal by the sample, a corrected set of ATR spectral data for the sample for output by the spectrometer to allow a determination of physical and/or chemical properties of the sample.

* * * * *